(12) United States Patent
Kohno (10) Patent No.: US 7,771,349 B2
(45) Date of Patent: Aug. 10, 2010

(54) ENDOSCOPE

(75) Inventor: Shinichi Kohno, Saitama (JP)

(73) Assignee: Fujinon Corporation, Saitama (JP)

( * ) Notice: Subject to any disclaimer, the term of this patent is extended or adjusted under 35 U.S.C. 154(b) by 392 days.

(21) Appl. No.: 11/094,181

(22) Filed: Mar. 31, 2005

(65) Prior Publication Data
US 2005/0222493 A1 Oct. 6, 2005

(30) Foreign Application Priority Data
Mar. 31, 2004 (JP) .............. P.2004-103370

(51) Int. Cl.
*A61B 1/00* (2006.01)
(52) U.S. Cl. .............. 600/107; 600/103; 600/104; 600/106
(58) Field of Classification Search ........... 600/103, 600/104, 106, 107, 109, 117, 129, 130, 153, 600/156, 157, 160, 462, 105
See application file for complete search history.

(56) References Cited

U.S. PATENT DOCUMENTS

| | | | | |
|---|---|---|---|---|
| 3,368,552 A | * | 2/1968 | Bottcher | 600/107 |
| 4,178,920 A | * | 12/1979 | Cawood et al. | 600/107 |
| 4,760,840 A | * | 8/1988 | Fournier et al. | 606/15 |
| 4,867,138 A | * | 9/1989 | Kubota et al. | 600/107 |
| 5,680,865 A | * | 10/1997 | Tanaka | 600/441 |
| 5,836,869 A | * | 11/1998 | Kudo et al. | 600/173 |
| 5,999,837 A | * | 12/1999 | Messner et al. | 600/407 |
| 6,238,336 B1 | * | 5/2001 | Ouchi | 600/160 |
| 6,390,973 B1 | * | 5/2002 | Ouchi | 600/113 |
| 6,409,666 B1 | * | 6/2002 | Ito | 600/439 |
| 6,458,074 B1 | * | 10/2002 | Matsui et al. | 600/106 |
| 6,824,509 B2 | * | 11/2004 | Yamaya et al. | 600/106 |
| 2002/0091303 A1 | * | 7/2002 | Ootawara et al. | 600/106 |
| 2003/0040657 A1 | * | 2/2003 | Yamaya et al. | 600/107 |

FOREIGN PATENT DOCUMENTS

| | | |
|---|---|---|
| EP | 0 069 942 A2 | 1/1983 |
| JP | 60-180401 | 11/1985 |
| JP | 09084747 A | 3/1997 |
| JP | 2002-034905 A | 2/2002 |

* cited by examiner

*Primary Examiner*—Linda C Dvorak
*Assistant Examiner*—Alireza Nia
(74) *Attorney, Agent, or Firm*—Rabin & Berdo, P.C.

(57) ABSTRACT

An endoscope comprises: an insertion portion that is to be inserted into a coelom; a treatment instrument elevation support, pivotally provided at a distal end of the insertion portion, that is used to guide a treatment instrument introduced at the distal end; and an observation section that obtains an image observed at the distal end, wherein, when the treatment instrument elevation support is reclined, part of the treatment instrument elevation support is included in the image obtained by the observation section.

15 Claims, 8 Drawing Sheets

ENDOSCOPE

BACKGROUND OF THE INVENTION

1. Field of the Invention

The present invention relates to an endoscope, and more in particular, to an endoscope that includes a treatment instrument elevation support for guiding a treatment instrument that is introduced via a treatment instrument insertion channel.

2. Description of the Invention

An endoscope roughly comprises: an insertion portion, to be inserted into a coelom; a control portion, connected to the base end of the insertion portion; and a connector, attached to the control portion by a cord. The insertion portion is constituted by connecting, in the named order from near the distal end, a head made of a hard material; a bending portion; and an introduction portion, which is the proximal end of the insertion portion. The head includes an observation portion, for observations performed inside a body; and a treatment instrument guide portion, for guiding a treatment instrument, which is inserted at the control portion, through a treatment instrument insertion channel.

In the treatment instrument guide portion, a treatment instrument is introduced through an opening that communicates with the treatment instrument insertion channel, and is guided in a predetermined direction by a treatment instrument elevation support. The treatment instrument elevation support is coupled with a wire that is connected to an elevation lever provided for the control portion, and can be rotated by using the elevation lever. The treatment instrument elevation support can be raised by using the elevation lever, and with the treatment instrument elevation support being up, in a predetermined direction, the treatment instrument can be stably guided. JP-UM-A-60-180401 is relevant to the present invention.

When the treatment instrument elevation support is elevated at a predetermined angle or greater, the distal end projects outward, beyond the outer circumference of the head. In this state, were the insertion portion to be inserted into or removed from the coelom, the projected treatment instrument elevation support would injure the surface of the coelom. Therefore, for safety, before the insertion or extraction of the insertion portion is performed, it must be confirmed that the treatment instrument elevation support is reclined.

A determination of whether the treatment instrument elevation support is reclined or is elevated, can be made by observing an image. According to the description of an endoscope disclosed in JP-UM-A-60-180401, when the treatment instrument elevation support is elevated, an image of at least part of the support can be captured in the observation view field.

With the structure described in JP-UM-A-60-180401, an image of part of the treatment instrument elevation support in the elevated state is included in the view field; however, when the treatment instrument elevation support is reclined, an image is not always captured in the view field. As is described above, the treatment instrument elevation support must be reclined when the insertion portion is inserted or removed, and there is a demand that the reclined state of the treatment instrument elevation support be properly confirmed before an insertion/removal operation is performed.

SUMMARY OF THE INVENTION

To resolve this problem, it is one objective of the present invention to provide an innovative and improved endoscope whereby it can be properly confirmed that a treatment instrument elevation support is reclined.

To achieve this objective, according to one aspect of the invention, an endoscope comprises: an insertion portion that is to be inserted into a coelom; a treatment instrument elevation support, pivotally provided at a distal end of the insertion portion, that is used to guide a treatment instrument introduced at the distal end; and an observation section that obtains an image observed at the distal end, wherein, when the treatment instrument elevation support is reclined, part of the treatment instrument elevation support is included in the image obtained by the observation section. With this arrangement, when the treatment instrument elevation support is reclined, this state can be always included in an image that is observed, so that the reclined state of the treatment instrument elevation support can be appropriately confirmed.

It is preferable that the endoscope further comprise: an identification section that employs the image to determine whether the treatment instrument elevation support has been reclined. With this arrangement, the identification section can be employed to easily determine whether the treatment instrument elevation support has been reclined.

The identification section may comprise a marker that is provided on the part of the treatment instrument elevation support, to determine whether the treatment instrument elevation support has been reclined, and that is captured in an image obtained when the treatment instrument elevation support is reclined. With this arrangement, when the marker is monitored in the image, whether the treatment instrument elevation support has been reclined can be easily ascertained.

The identification section may further comprise a position indicator that designates a location of the marker that is displayed in the image when the treatment instrument elevation support is reclined. With this arrangement, when the locations of the position indicator and the marker match, it is determined that the treatment instrument elevation support has been reclined. In this manner, identification of the state can more exactly be performed.

In an elevated state of the treatment instrument elevation support, part of the treatment instrument elevation support may be included in the image obtained by the observation portion, and the identification section further comprises: a reclined position indicator that indicates a first position of the marker that is displayed in the image when the treatment instrument elevation support is reclined; and an elevation position indicator that indicates a second position of the marker that is displayed in the image when the treatment instrument elevation support is elevated. With this arrangement, part of the treatment instrument elevation support is included in the image either when the support has been elevated or reclined, and the state of the treatment instrument elevation support can be clearly ascertained.

BRIEF DESCRIPTION OF THE INVENTION

The preferred embodiments of the present invention will now be described in detail while referring to the accompanying drawings. In this specification and the drawings, the same reference numerals are used to denote components having substantially the same functions, and repetitive explanations will not be given for them.

Figure 1:
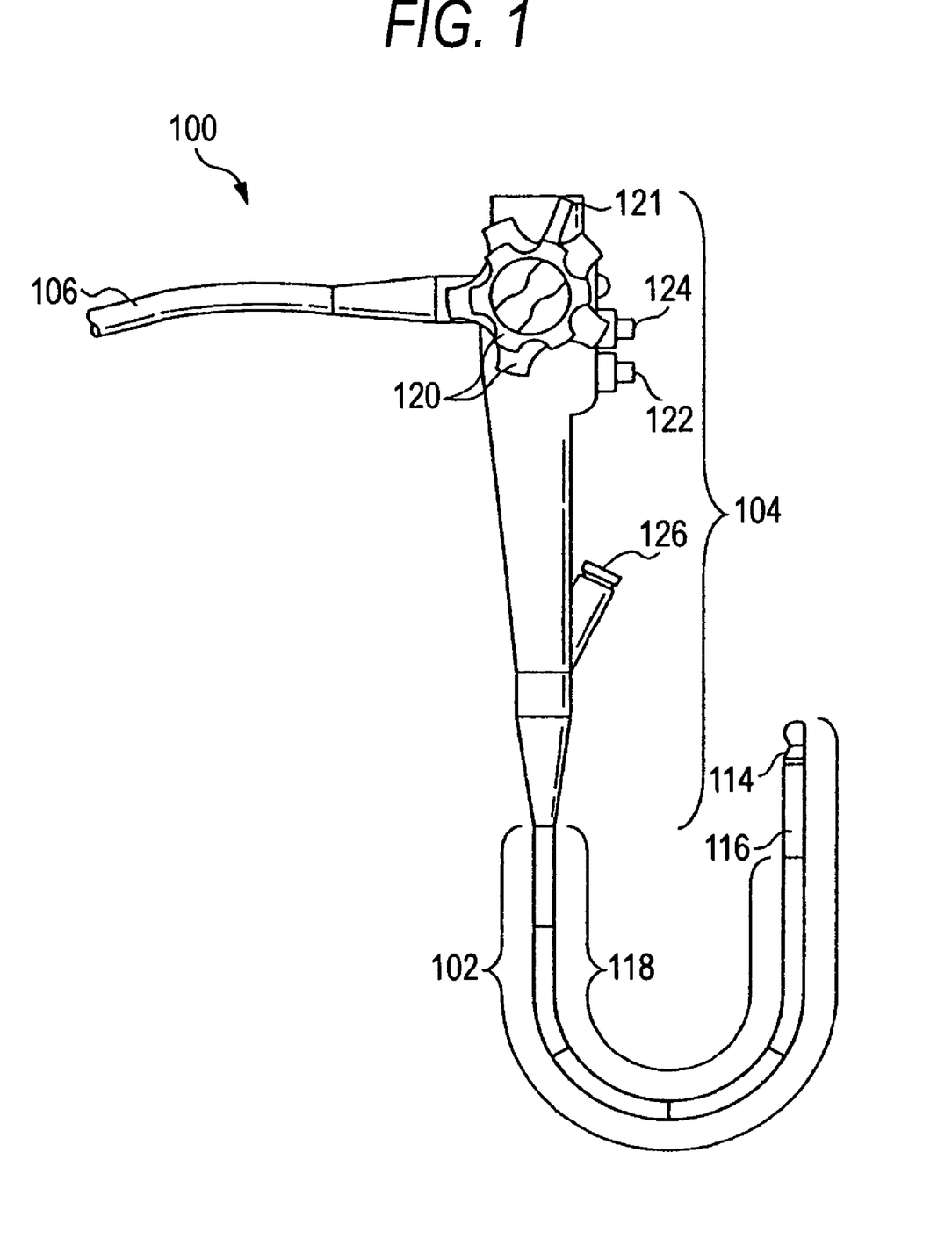
FIG. 1 is a schematic diagram showing the structure of an endoscope according to a first embodiment of the present invention.

An ultrasonic endoscope 100 according to a first embodiment of the invention will now be explained while referring to FIG. 1. While an ultrasonic endoscope is employed in the following embodiments, the present invention is not limited to an ultrasonic endoscope, and can also be applied for a common endoscope. FIG. 1 is a schematic diagram showing the structure of the ultrasonic endoscope 100 according to the first embodiment. The ultrasonic endoscope 100 comprises: an elongated and flexible insertion portion 102 to be inserted into a coelom; a control portion 104 connected to the proximal end of the insertion portion 102; a universal cord 106 extended from the side of the control portion 104; and a connector (not shown) provided at the distal end of the universal cord 106 and connected to a light source or an ultrasonic observation apparatus (neither of them shown) The connector may be connected to an image processing apparatus or to a display device such as a monitor (neither of which is shown).

The insertion portion 102 is constituted by connecting, in the named order and from near the distal end, a head 114 that consists of a hard resin member, a bending portion 116 that is bendable and is located at the proximal end of the head 114, and a long and flexible introduction portion 118, having a small diameter, that extends from the proximal end of the bending portion 116 to the distal end of the control portion 104.

The control portion 104 includes: an angle knob 120, for bending the bending portion 116 in a desired direction; an elevation lever 121, for elevating a treatment instrument elevation support; an air/water button 122, for supplying air and water used to clean the windows of an observation portion and a lighting portion that are provided for the head 114; and a suction button 124, for performing a suction operation.

A treatment instrument insertion port 126 is provided on the side of the control portion 104, near the distal end, for the insertion of a treatment instrument, such as forceps, into a target portion in a coelom. The treatment instrument insertion port 126 communicates with a treatment instrument insertion channel (not shown in FIG. 1) that is extended inside the insertion portion 102 and that communicates with the opening of a treatment instrument guide portion (not shown in FIG. 1) provided for the head 114.

Figure 2:
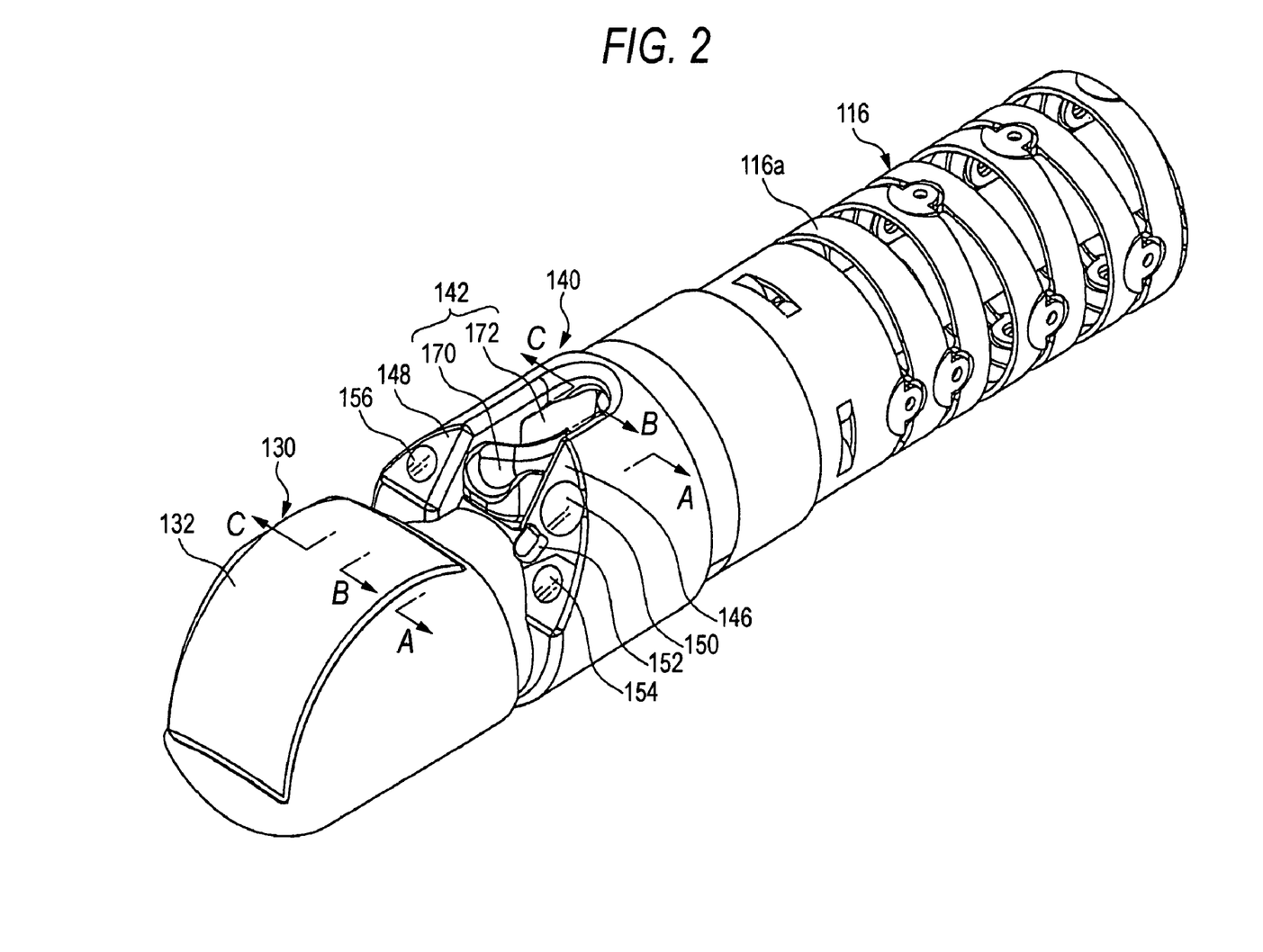
FIG. 2 is a perspective view of the structures of the head and the bending portion of the endoscope according to the first embodiment.
Figure 3:
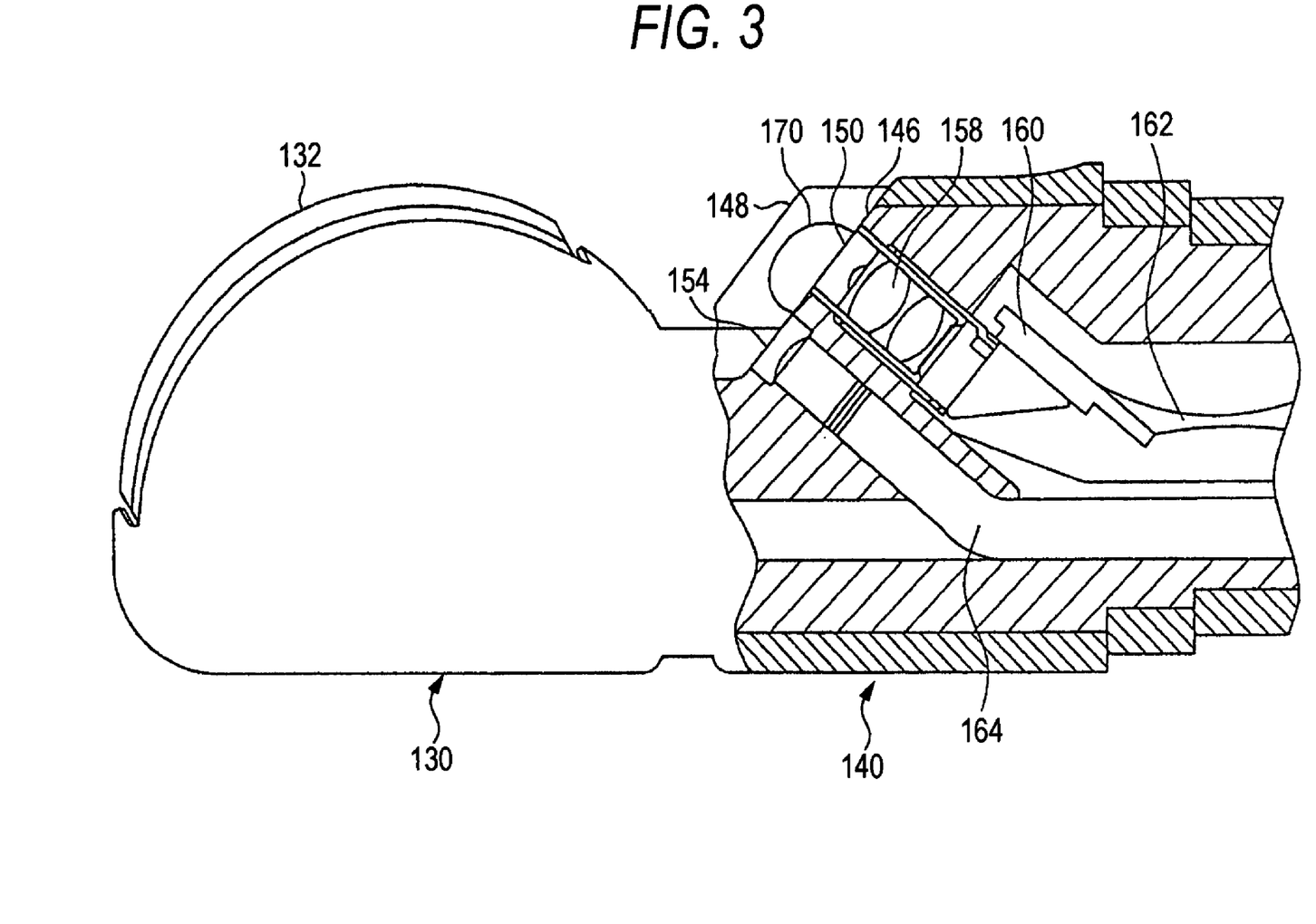
FIG. 3 is a partially cut away side view of the head at position A-A in FIG. 2.

The structures of the head 114 and the bending portion 116 will now be described while referring to FIGS. 2 to 4. FIG. 2 is a perspective view of the structures of the head 114 and the bending portion 116 of the ultrasonic endoscope 100 in this embodiment. FIGS. 3, 4A and 4B are partially cut away side views of the head 114 at positions A-A, B-B and C-C in FIG. 2.

As is shown in FIG. 2, the bending portion 116 has a joint ring structure wherein a plurality of joint rings 116a are sequentially connected in the axial direction. Inside the joint rings 116a, arranged at predetermined intervals in the axial direction of the inner wall, are multiple operation wires, the proximal ends of which are connected to a pulley (not shown) that is rotated by the angle knob 120 of the control portion 104. With this structure, when the pulley is turned by manipulating the angle knob 120, the operation wires are pulled and bend the bending portion 116 in a desired direction.

The head 114 is constituted by connecting an ultrasound test mechanism 130, provided near the distal end, and an endoscopic observation mechanism 140, provided nearer the proximal end than the ultrasound test mechanism 130. The ultrasound mechanism 130 is, for example, an ultrasonic oscillation testing mechanism that includes an ultrasound transducer 132 for examining the state of internal tissue. The ultrasound transducer 132 has, for example, a convex structure where in multiple rectangular ultrasonic oscillators, for the transmission and reception of ultrasonic waves, are convexly arranged.

A treatment instrument guide portion 142 for guiding a treatment instrument is provided in the center of the upper face of the endoscopic observation mechanism 140, and an observation portion, which obtains an image observed by the head 114, and first and second lighting portions are provided on either side of the treatment instrument guide portion 142. For the ultrasonic endoscope 100, multiple lighting portions are provided in order to reduce uneven lighting. The structure of the endoscopic observation mechanism 140 will now be described in detail.

Viewed from the distal end of the head 114 in the axial direction, a first tilted face 146 and a second tilted face 148, which rise obliquely upward toward the distal end, are formed on the right and left sides of the treatment instrument guide portion 142. As is shown in FIG. 2, in the first tilted face 146, from the top, an observation window 150, an air/water supply port 152 and a first lighting window 154 are formed in the named order, and in the second tilted face 148, a second lighting window 156 is formed.

The observation window 150 is used to obtain an image of what is being observed, and constitutes the end face of the observation portion of the ultrasonic endoscope 100. As is shown in FIG. 3, the observation portion includes: the observation window 150; an object lens 158, located inside the observation window 150; a CCD (Charge Coupled Device) 160, which is a solid-state imaging device located at a focal position for the object lens 158; and an electric wire 162, connected to the CCD 160.

The air/water supply port 152 is a nozzle opening through which air is fed or a cleaner is sprayed to clean the observation window 150.

The first lighting window 154 is a window through which light is emitted to illuminate an observed portion in the field of view, and constitutes the end face of the first lighting portion. As is shown in FIG. 3, the first lighting portion includes the first lighting window 154 and a light guide 164, which is an optical fiber bundle located inside the first lighting window 154. The light guide 164, which is passed through the control portion 104 and the universal cord 106, is connected to a light source and transmits light emitted by the light source to the first lighting window 154.

The second lighting window 156 is a window through which light is emitted to illuminate an observed portion in the field of view, and constitutes the end face of the second lighting portion. The second lighting portion also includes a light guide, and is structured the same as the first lighting portion. In this embodiment, the second lighting window 156 is projected farther towards the distal end than is the observation window 150 in the first tilted face 146. However, the structural arrangement is not limited to this, and the second lighting window 156 and the observation window 150 can be arbitrarily positioned.

As is described above, all of the observation window 150, the first lighting window 154 and the second lighting window 156 that are arranged in the individual tilted faces are directed obliquely upward toward the distal end at substantially the same tilting angle relative to the axial direction of the head 114. With this structure, the observation direction for the observed portion and the directions in which light is emitted by the first and second lighting portions are also obliquely upward toward the distal end, and the light axial direction of the field of view substantially matches the light axial direction of the emitted light. Since the light axial direction is aligned in this embodiment, lighting can be efficiently performed.

The treatment instrument guide portion 142 will now be described while referring to FIGS. 4A and 4B. The treatment instrument guide portion 142 mainly includes: a treatment instrument elevation support 170, which can be freely elevated or reclined in order to guide a treatment instrument in a predetermined direction; and an elevation support storage space 172, which is recessed, for storing the treatment instrument elevation support 170. Part of the proximal end of the elevation support storage space 172 is an opening, and as is shown in FIG. 4A, communicates with a treatment instrument insertion channel 174.

Figure 4A:
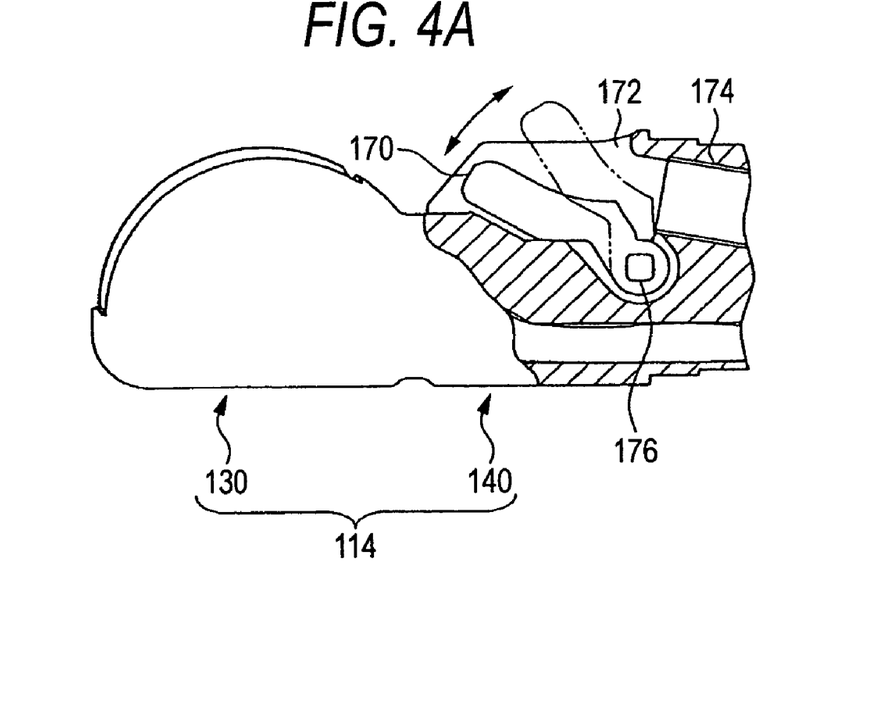
FIG. 4A is a partially cut away side view of the head at position B-B in FIG. 2.
Figure 4B:
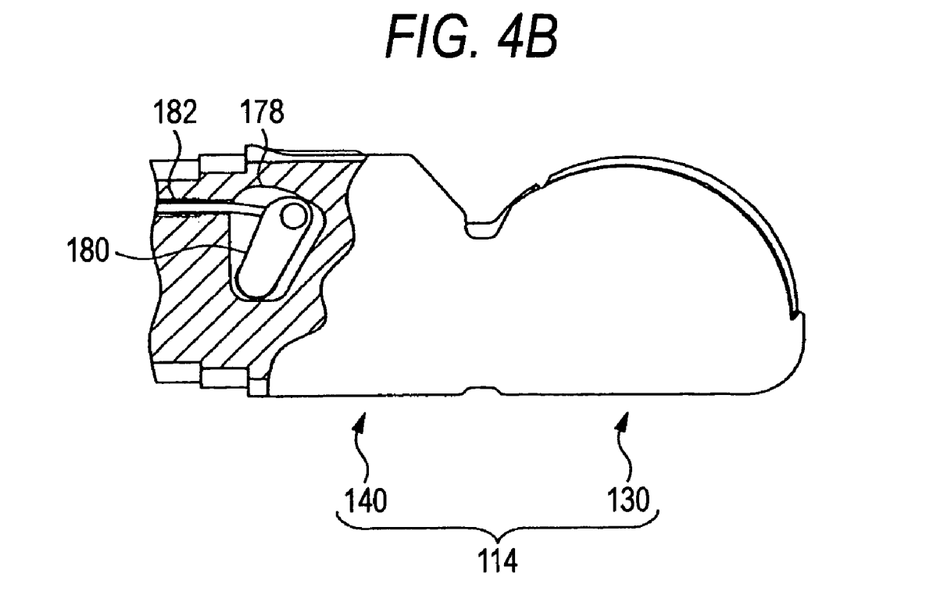
FIG. 4B is a partially cut away side view of the head at position C-C in FIG. 2.

The upper face of the treatment instrument elevation support 170 is a guide face for guiding a treatment instrument, and, as is shown in FIG. 4A, the proximal end is pivotally supported at a shaft 176 that is attached, almost vertically, to the shaft of the head 114. The shaft 176 is connected to the arched lower end of a coupling member 180 having an almost elliptic shape shown in FIG. 4B, which is arranged in the axial direction of the shaft 176 at a predetermined distance from the treatment instrument elevation support 170. The coupling member 180 is pivotally positioned in a guide groove 178 having an almost fan shape, and an operation wire 182 is connected to the upper portion of the coupling member 180. By pulling or pushing the operation wire 182, the arched lower end of the coupling member 180 is slid across the inner wall of the guide groove 178, and is pivoted along the contact face. The operation wire 182 is connected to the elevation lever 121 provided for the control portion 104, and is pulled or pushed by manipulating the elevation lever 121.

The raising and the reclining of the treatment instrument elevation support 170 can be performed by manipulating the elevation lever 121. For example, in the state in FIG. 4B, when the operation wire 182 is pulled by manipulating the elevation lever 121, the coupling member 180 is turned, and accordingly, the shaft 176 is rotated and the treatment instrument elevation support 170 is elevated. The angle of elevation of the treatment instrument elevation support 170 can be adjusted and corresponds to the degree to which the elevation lever 121 is turned.

In FIG. 4A, the state wherein the treatment instrument elevation support 170 is up is indicated by a double-doted chain line, and the state wherein the support 170 is reclined is indicated by a solid line. In the reclined state, the treatment instrument elevation support 170 is brought into contact with the bottom of the elevation support storage space 172, and the distal end of the support 170 is located at the lowest position within the pivoting range. At this time, the treatment instrument elevation support 170 is stored completely in the elevation support storage space 172, and does not project outward beyond the outer circumference of the head 114. Further, as is apparent from FIG. 4A, when the treatment instrument elevation support 170 is raised at a predetermined angle or greater, the distal end of the support 170 projects outward beyond the outer circumference of the head 114. When the insertion portion 102 is inserted or removed in this state, the surface of the body would be damaged. Therefore, before inserting or extracting the insertion portion 102, the treatment instrument elevation support 170 should be reclined. Only after this state has been confirmed, should the insertion/extraction be performed.

Figure 5A:
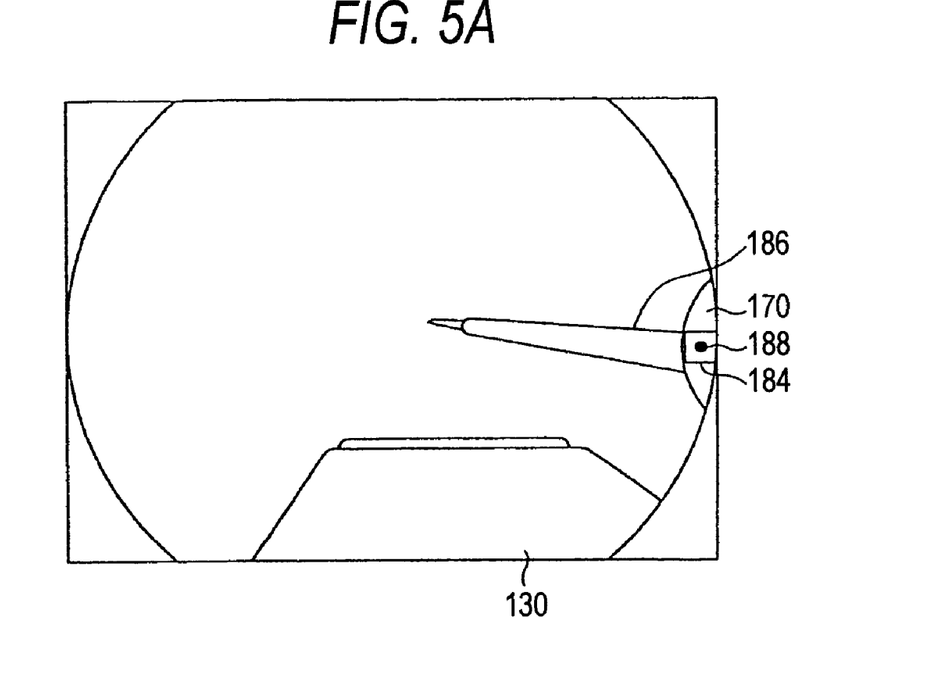
FIGS. 5A and 5B are specific diagrams respectively showing images observed by the endoscope according to the first embodiment in the elevated state and in the reclined state.
Figure 5B:
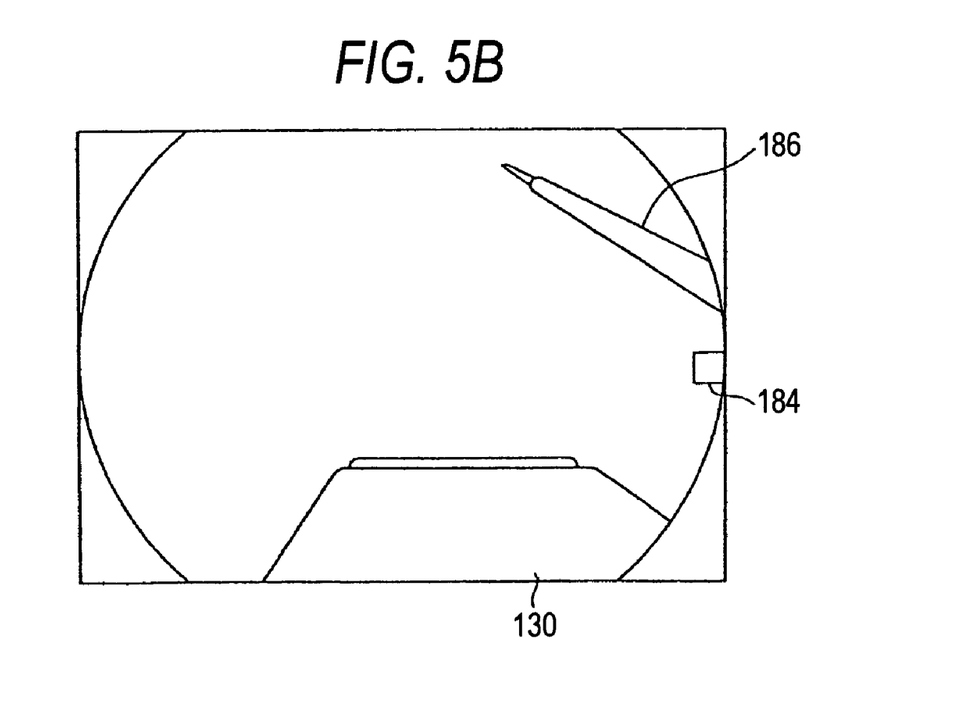

Therefore, the ultrasonic endoscope 100 of this embodiment is designed so that, when the treatment instrument elevation support 170 has been reclined, part of the treatment instrument elevation support 170 is captured in an image observed by the observation portion. While referring to FIGS. 5A and 5B, an explanation will now be given for an image observed when the treatment instrument elevation support 170 has been reclined and when the elevation support 170 has been raised. FIGS. 5A and 5B are specific diagrams showing images observed by the ultrasonic endoscope 100 of this embodiment. The state shown in FIG. 5A is the one obtained when the treatment instrument elevation support 170 has been reclined, and the state in FIG. 5B is the one obtained when it has been raised.

In this embodiment, a rectangular position indicator 184 is displayed in the center on the right side of an observed image that is shaped by removing the upper and lower ends of a circle. The position indicator 184 may be displayed by forming a mask image using an image processing apparatus, or by employing a focusing glass, such as a reticle. Furthermore, for the ultrasonic endoscope 100 of this embodiment, one part of the ultrasound test mechanism 130 is included in the observed image, so that the portion currently being examined can be confirmed in the observed image.

Apparent from FIG. 5A, a part of the treatment instrument elevation support 170 in the reclined state is displayed in the center to the right of the observed image, a treatment instrument 186 is projected, and a circular marker 188 is positioned in the position indicator 184. The marker 188 is provided in a part of the treatment instrument elevation support 170 that is to be entered in the observed image in the reclined state. The marker 188 is used to determine, based on an observed image, whether the treatment instrument elevation support 170 is reclined.

Figure 6:
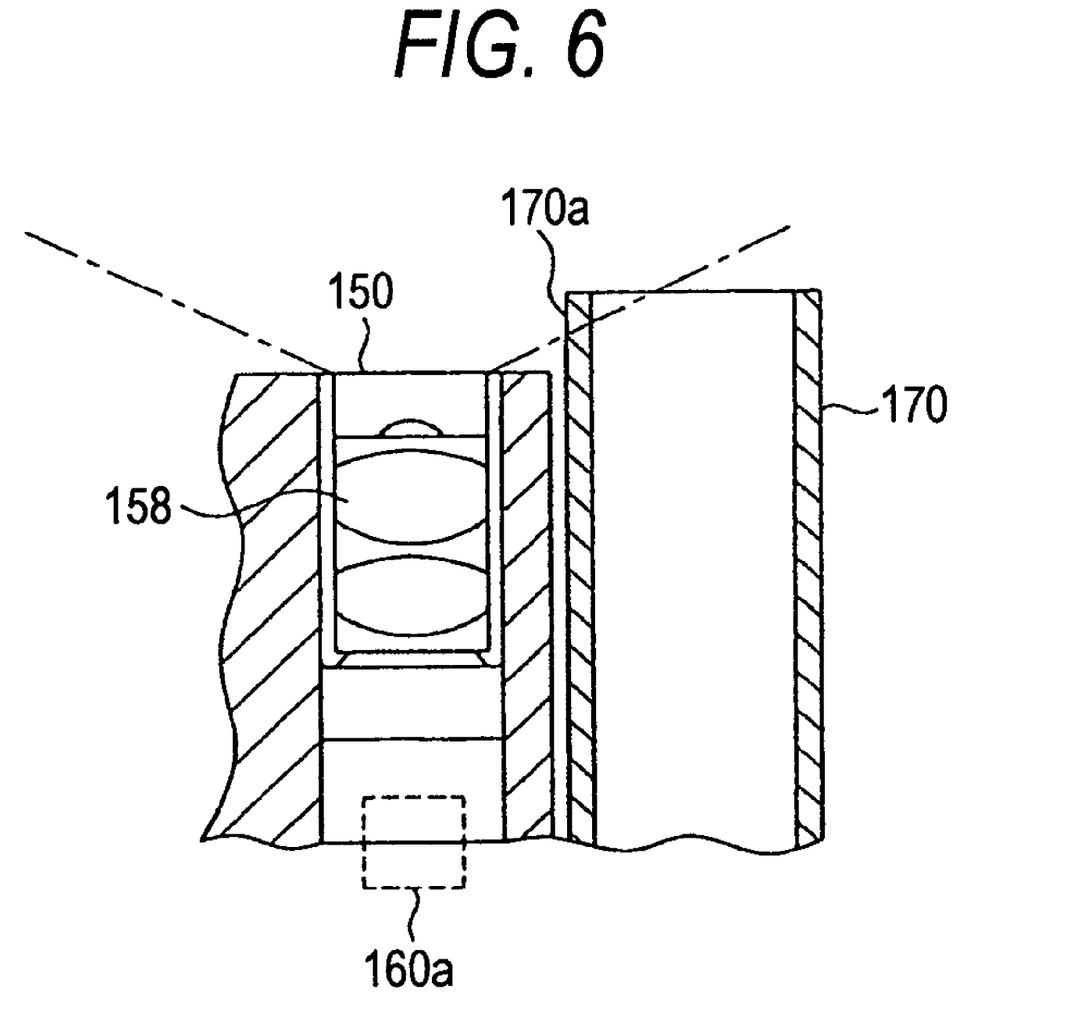
FIG. 6 is a cross-sectional view of the vicinity of the distal end of the treatment instrument elevation support of the endoscope according to the first embodiment.

As is shown in FIG. 6, the marker 188 can be located at a distal end 170a of the treatment instrument elevation support 170, nearer the observation portion. FIG. 6 is a cross-sectional view of the structure that includes the light axis of the observation portion and the longitudinal axis of the treatment instrument elevation support 170. An imaging face 160a of the CCD 160 is indicated by a broken line, and the observation field of view through the observation window 150 is indicated by a dotted chain line.

In FIG. 5B, the treatment instrument 186 is entered in the observed image, and the treatment instrument elevation support 170 in the elevated state and the marker 188 are not seen. As is described above, according to the embodiment, in the elevated state, the treatment instrument elevation support 170 is not entered in the observed image, and in the reclined state, a part of the elevation support 170 is entered in the observed image and the marker 188 is located in the position indicator 184. That is, the position indicator 184 represents the location of the marker 188 in the observed image when the treatment instrument elevation support 170 is reclined, and is an identification portion, based on the observed image, used to determine whether the treatment instrument elevation support 170 is reclined.

By referring to FIGS. 5A and 5B, whether the treatment instrument elevation support 170 has been reclined can be easily ascertained by examining the presence/absence of the elevation support 170 in the observed image, and the presence/absence of the marker 188 in the position indicator 184. Therefore, according to this embodiment, it can be precisely confirmed that the treatment instrument elevation support 170 has been reclined, and the safety for the insertion and extraction of the insertion portion 102 can be increased.

After the treatment instrument elevation support 170 in the reclined state in FIG. 4A, indicated by a solid line, is elevated, a part of the treatment instrument elevation support 170 and the marker 188 may be seen in the image observed until the entire elevation support 170 is reclined into the elevation support storage space 172 and does not project outward beyond the outer circumference of the head 114. With this arrangement, so long as part of the treatment instrument elevation support 170 and the marker 188 can be confirmed in the image observed, the treatment instrument elevation support 170 is not projected outward beyond the outer circumference of the head 114, so that the insertion and extraction of the insertion portion 102 are enabled.

A second embodiment of the present invention will now be described. An ultrasonic endoscope for the second embodiment is substantially the same as the one for the first embodiment, with the exception that, in the second embodiment, part of a treatment instrument elevation support 270 is seen in an image observed both in the raised state and the laid-down state, so that the state of the elevation support 270 can be identified based on the image observed. Only that which differs from the first embodiment will be explained, and no further explanation will be given for corresponding structures.

Figure 7A:
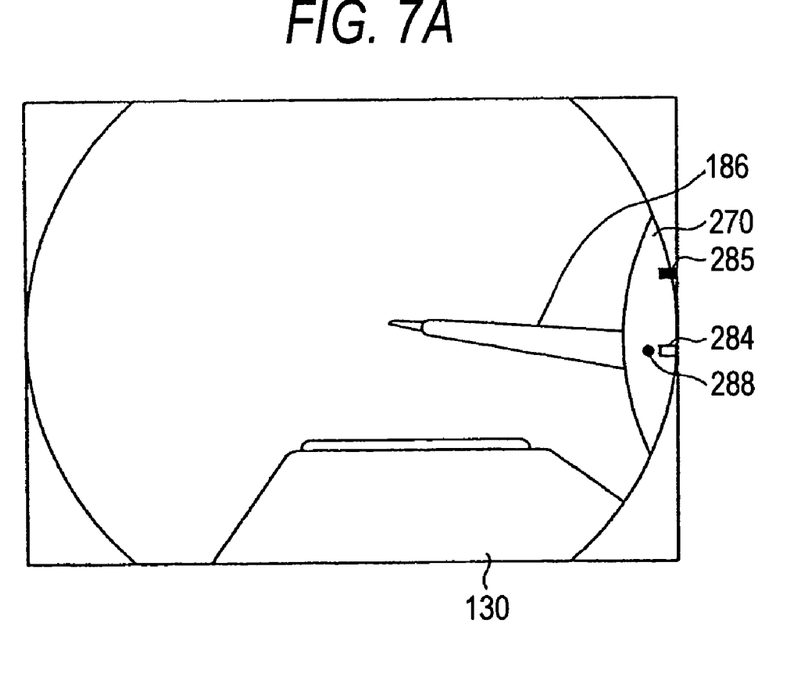
FIGS. 7A and 7B are specific diagrams respectively showing images observed by an endoscope according to a second embodiment in the elevated state and in the reclined state.
Figure 7B:
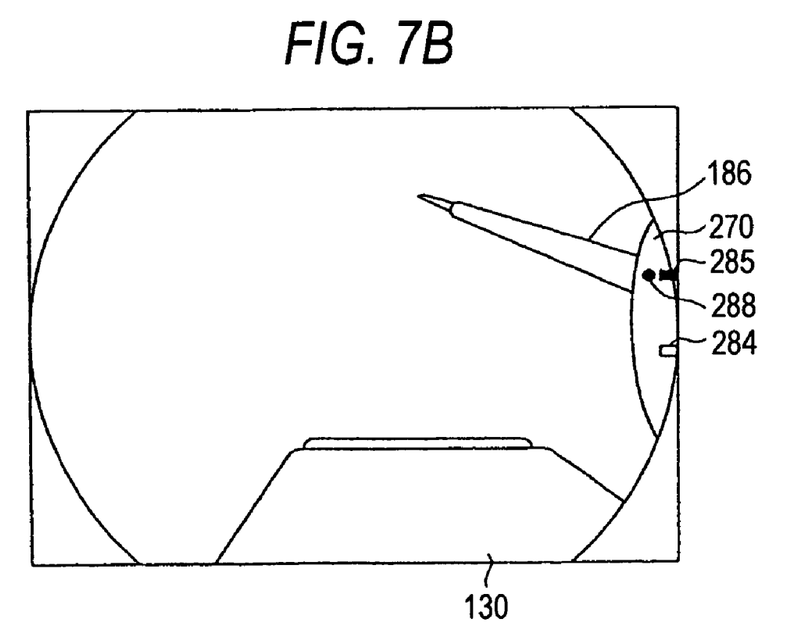

For this embodiment, images observed when the treatment instrument elevation support 270 is elevated and reclined will be described while referring to FIGS. 7A and 7B. FIGS. 7A and 7B are specific diagrams showing images observed by the ultrasonic endoscope of this embodiment. The image in FIG. 7A is obtained when the treatment instrument elevation support 270 is reclined, and the image in FIG. 7B is obtained when the elevation support 270 is elevated. In this embodiment, in the center on the right of an image shaped like a circle with the upper and lower ends removed, two differently colored bar-shaped position indicators 284 and 285 are displayed vertically at a predetermined distance. The position indicators 284 and 285 are formed and displayed in the same manner as is the position indicator 184 for the first embodiment. Also in this embodiment, part of the ultra sound test mechanism 130 is displayed so that the portion currently being examined is confirmed in the image observed.

As is apparent from FIG. 7A, one part of the treatment instrument elevation support 270 in the reclined state is seen in the center on the right of the image observed, and the treatment instrument 186 is projected. Further, a circular marker 288, which is provided in part of the treatment instrument elevation support 270, is located immediately on the left of the lower position indicator 284. In FIG. 7B, one part of the treatment instrument elevation support 270 in the raised state is seen in the center on the right of the observed image, and the circular marker 288 is located immediately to the left of the upper position indicator 285.

That is, the position indicator 284 is a reclined position indicator that indicates the location of the marker 288 that is seen in an image observed when the treatment instrument elevation support 270 is reclined. The position indicator 285 is a raised position indicator that indicates the location of the marker 288 that is seen in an image observed when the treatment instrument elevation support 270 is elevated. The marker 288 and the position indicators 284 and 285 function as an identification section for determining, based on the image observed, whether the treatment instrument elevation support 270 is reclined. As is described above, in this embodiment wherein, both in the elevated state and the reclined state, part of the treatment instrument elevation support 270 is seen in the image observed, it can also be precisely confirmed, based on the image observed, that the treatment instrument elevation support 270 is reclined, and the safety for the insertion and the extraction of the insertion portion can be increased.

The preferred embodiments of the present invention have been described while referring to the accompanying drawings. However, the present invention is not limited to these embodiments. It will be obvious to one having ordinary skill in the art that the present invention can be variously modified or altered within the scope described in the claims, and it can be understood that these modifications or alterations belong to the technical scope of the invention.

The colors and shapes of the marker and the position indicators are not limited to those in the embodiments, and can be arbitrarily designated. For example, green may be employed as the color for the position indicator 284 that indicates the position of the treatment instrument elevation support in the reclined state, and red may be employed for the position indicator 285 that indicates the position of the treatment instrument elevation support in the elevated state.

An ultrasonic endoscope has been employed for the embodiments. However, the present invention is not limited to this, and can also be applied for a common endoscope that does not include an ultrasound test mechanism.

For an ultrasonic endoscope, multiple wires are led out of an ultrasonic testing mechanism and extended below the treatment instrument guide portion of an endoscope observation mechanism. In order to obtain space for these wires, the treatment instrument storage space of the ultrasonic endoscope is formed so it is shallower than is one for a common endoscope, so that the treatment instrument elevation support tends to be projected outward beyond the outer circumference of the head. For this reason, applying the present invention for an ultrasonic endoscope is very effective.

Recently, in order to reduce the load imposed on a patient, a reduction in the diameter of an insertion portion has also been for a common endoscope, and the diameter of the head also tends to be reduced. On the other hand, a specific distance in the axial direction is required for the treatment instrument elevation support in order to guide a treatment instrument, so that as the diameter of the endoscope is reduced, the treatment instrument elevation support for the endoscope is more likely to be projected outward beyond the outer circumference of the head, as with the ultrasonic endoscope. Therefore, as the reduction of the diameter is continued, the problem described for the invention can not be disregarded even for a common endoscope, and use of the present invention becomes effective.

Figure 8:
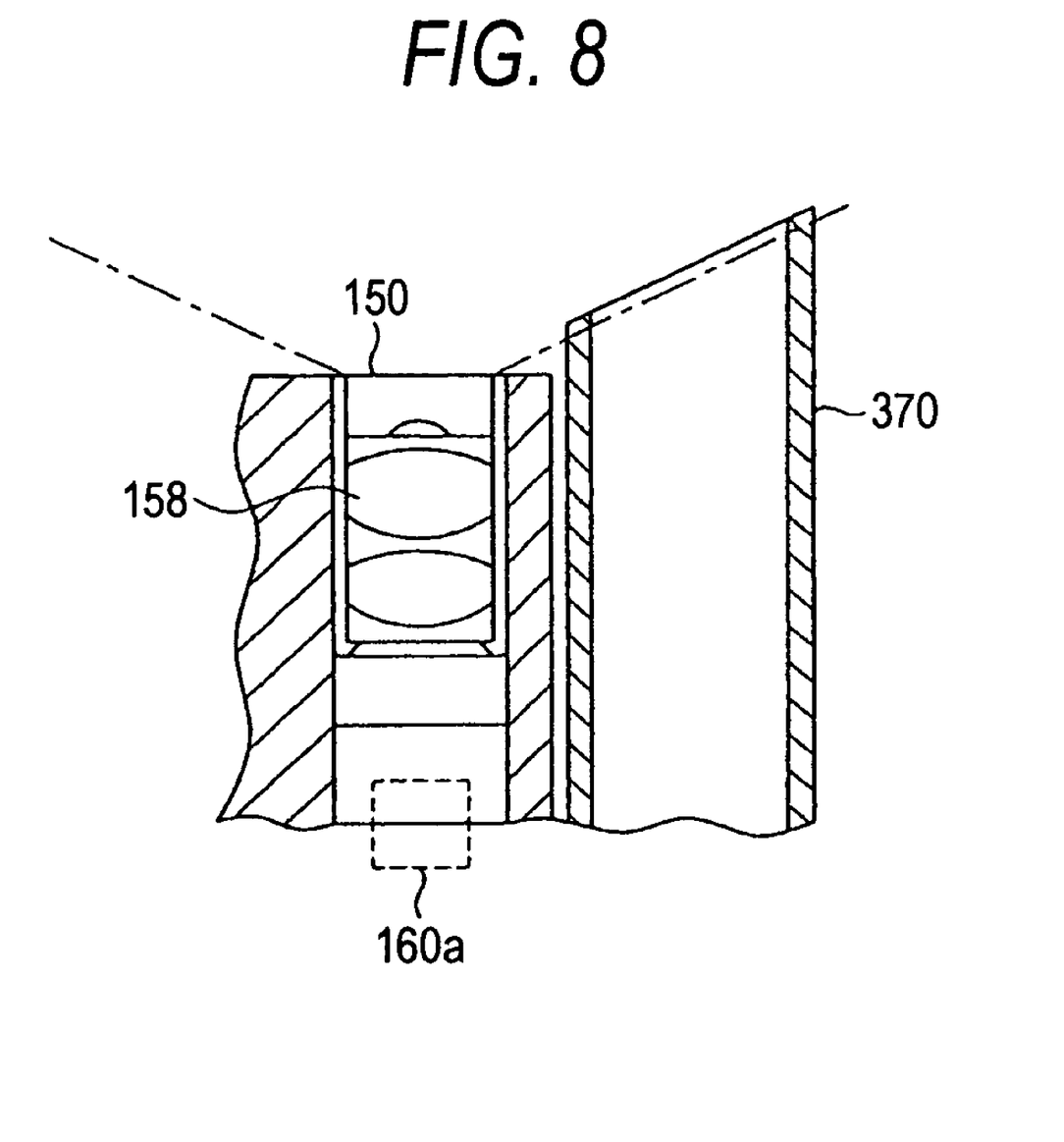
FIG. 8 is a cross-sectional view of the vicinity of the distal end of the treatment instrument elevation support of the endoscope according to a modification of the invention.

The shape of the distal end of the treatment instrument elevation support is not limited to that shown in FIG. 6, and as is shown in FIG. 8, the distal end may be formed along the angle of the observation field of view. FIG. 8 is a cross-sectional view of the structure, including the light axis of the observation portion and the longitudinal axis, of a treatment instrument elevation support 370. The imaging face 160a of the CCD 160 is indicated by a broken line, and the viewing range through observation window 150 is indicated by a dotted chain line. In this case, there is an advantage in that the moment whereat the treatment instrument begins to be guided from the treatment instrument elevation support 370 can be observed.

A biopsy tool having a sharp distal end is especially employed for the ultrasonic endoscope. So long as the moment whereat the biopsy tool begins to be guided from the treatment instrument guidance portion can be observed, the direction in which the biopsy tool is guided can be confirmed, and the position of the biopsy tool can be precisely adjusted before it reaches a diseased part.

As is described above, according to the endoscope of the invention, an image that is observed can be employed to easily ascertain whether the treatment instrument elevation support has been reclined. Thus, for the insertion and removal of the insertion portion, the safety can be increased.

The present invention can be applied for an endoscope wherein a treatment instrument elevation support for guiding a treatment instrument is provided at the head of an insertion portion.

The entire disclosure of each and every foreign patent application from which the benefit of foreign priority has been claimed in the present application is incorporated herein by reference, as if fully set forth.

What is claimed is:

1. An endoscope comprising:
   an insertion portion that is to be inserted into a coelom;
   a treatment instrument elevation support, pivotally provided at a distal end of the insertion portion, that is used to guide a treatment instrument introduced at the distal end;
   an observation section that obtains an image observed at the distal end, the observation section including a lens; and
   an identification section that employs the image to determine whether the treatment instrument elevation support has been reclined;
   wherein the observation section is provided on a side of the treatment instrument elevation support, and
   wherein the treatment instrument elevation support and the observation section are disposed in such a positional relationship that, when the treatment instrument elevation support is reclined, a part of the treatment instrument elevation support is included in the image obtained by the observation section, and
   wherein the identification section comprises a marker provided on the part of the treatment instrument elevation support, to determine whether the treatment instrument elevation support has been reclined, such that the marker is captured in the image obtained when the treatment instrument elevation support is reclined, and
   wherein the endoscope is configured to define an elevation support storage space for storing the treatment instrument elevation support.

2. The endoscope according to claim 1,
   wherein the identification section further comprises:
   a position indicator that designates a location of the marker that is displayed in the image when the treatment instrument elevation support is reclined.

3. The endoscope according to claim 1,
   wherein, in an elevated state of the treatment instrument elevation support, at least a part of the treatment instrument elevation support is included in the image obtained by the observation section; and
   wherein the identification section further comprises:
   a reclined position indicator that indicates a first position of the marker that is displayed in the image when the treatment instrument elevation support is reclined; and
   an elevation position indicator that indicates a second position of the marker that is displayed in the image when the treatment instrument elevation support is elevated.

4. The endoscope according to claim 1, wherein the elevation support storage space includes an opening through which the treatment instrument elevation support passes inwardly when it is reclined and passes outwardly when it is elevated.

5. The endoscope according to claim 4, wherein:
   the treatment instrument elevation support is elevated or reclined in order to guide the treatment instrument;
   when reclined, the treatment instrument elevation support is completely stored in the elevation support storage space; and
   when elevated, a distal end of the treatment instrument elevation support passes outwardly through the opening, and projects beyond the elevation support storage space.

6. The endoscope according to claim 1, wherein:
   the insertion portion has a tilted face rising obliquely upward toward the distal end; and
   the observation section includes an observation window formed on the tilted face.

7. The endoscope according to claim 1, wherein when the treatment instrument elevation support is elevated, no part of the treatment instrument elevation support is included in the image obtained by the observation section.

8. The endoscope according to claim 1, the lens is provided on a tip portion of the observation section.

9. The endoscope according to claim 1, wherein when the treatment instrument elevation support is reclined, a guide direction of the treatment instrument elevation support is substantially parallel to the light axis direction of the lens of the observation section.

10. The endoscope according to claim 1, wherein the insertion portion has a first tilted face and a second tilted face, and the observation section includes an observation window formed on the first tilted face, and
    wherein when the treatment instrument elevation support is reclined, a top end of the treatment instrument elevation support projects toward the light axis direction from the first tilted face so that the part of the treatment instrument elevation support is included in the image obtained by the observation section.

11. An endoscope comprising:
    an insertion portion that is to be inserted into a coelom;
    a treatment instrument elevation support, pivotally provided at a distal end of the insertion portion, that is used to guide a treatment instrument introduced at the distal end; and
    an observation section that obtains an image observed at the distal end,
    wherein the treatment instrument elevation support and the observation section are disposed in such a positional relationship that, when the treatment instrument elevation support is reclined, a part of the treatment instrument elevation support is included in the image obtained by the observation section, and
    wherein the endoscope is configured to define an elevation support storage space for storing the treatment instrument elevation support,
    wherein:
    the insertion portion has a first tilted face and a second tilted face, both rising obliquely upward toward the distal end, the second tilted face being spaced apart from the first tilted face, the elevation support storage space being defined between the first and second tilted face, the second tilted face, taken from a side view of the endoscope, is disposed at an upper-forward position with respect to the first tilted face;

the treatment instrument elevation support is stored in the elevation support storage space; and the observation section includes an observation window formed on the first tilted face, through which the observation section obtains the image, the observation window having an observation field of view, the observation window being disposed at such a position on the first tilted face that, when the treatment instrument elevation support is reclined, said part of the treatment instrument elevation support is disposed within the observation field of view of the observation window.

12. The endoscope according to claim 11, wherein the treatment instrument elevation support is stored in the elevation support storage space, such that said part, taken from the side view of the endoscope, is disposed between the first and second tilted faces.

13. The endoscope according to claim 12, wherein, the treatment instrument elevation support is stored in the elevation support storage space, such that at least a portion of the treatment instrument elevation support, taken from the side view of the endoscope, passes outwardly through and projects beyond a first imaginary plane that includes the first tilted face and extends in a direction toward a second imaginary plane that includes the second tilted face.

14. The endoscope according to claim 13, wherein a distal end of the treatment instrument elevation support, taken from the side view of the endoscope, is disposed between the first and second tilted faces.

15. The endoscope according to claim 14, wherein a distal end of the treatment instrument elevation support is shaped, when the treatment instrument elevation support is stored in the elevation support storage space, to be in parallel with a line that forms a boundary of the observation field of view of the observation window.

* * * * *